(12) United States Patent
Pluyter et al.

(10) Patent No.: US 9,126,890 B2
(45) Date of Patent: Sep. 8, 2015

(54) LOW VOLATILE REACTIVE MALODOR COUNTERACTIVES AND METHODS OF USE THEREOF

(75) Inventors: Johan Gerwin Lodewijk Pluyter, Middletown, NJ (US); Takashi Sasaki, Belford, NJ (US); Xiao Huang, Freehold, NJ (US)

(73) Assignee: International Flavors & Fragrances Inc. NY (US)

( * ) Notice: Subject to any disclaimer, the term of this patent is extended or adjusted under 35 U.S.C. 154(b) by 0 days.

(21) Appl. No.: 13/277,288

(22) Filed: Oct. 20, 2011

(65) Prior Publication Data

US 2013/0101544 A1    Apr. 25, 2013

(51) Int. Cl.
| | |
|---|---|
| *C07C 205/44* | (2006.01) |
| *C07C 223/06* | (2006.01) |
| *C07C 323/22* | (2006.01) |
| *A61L 9/01* | (2006.01) |

(52) U.S. Cl.
CPC ............. *C07C 205/44* (2013.01); *C07C 223/06* (2013.01); *C07C 323/22* (2013.01); *A61L 9/01* (2013.01); *C07B 2200/11* (2013.01)

(58) Field of Classification Search
CPC combination set(s) only.
See application file for complete search history.

(56) References Cited

U.S. PATENT DOCUMENTS

| | | | |
|---|---|---|---|
| 5,037,412 A | 8/1991 | Tanzer et al. | |
| 5,288,802 A * | 2/1994 | Walters et al. | 525/110 |
| 5,601,809 A | 2/1997 | Davis | |
| 5,719,231 A * | 2/1998 | Famili | 525/61 |
| 5,769,832 A | 6/1998 | Hasse | |
| 6,376,741 B1 | 4/2002 | Guarracino et al. | |
| 6,379,658 B1 | 4/2002 | Marano et al. | |
| 6,403,075 B1 | 6/2002 | Costa | |
| 6,610,648 B2 | 8/2003 | McGee et al. | |
| 7,585,833 B2 | 9/2009 | Fadel et al. | |
| 2002/0058017 A1 | 5/2002 | Tajima et al. | |
| 2012/0101187 A1* | 4/2012 | Kuo et al. | 523/335 |

OTHER PUBLICATIONS

Sutherland, Biochem. J. (1969) 115, 935-945.*
Lee et al., J. of Biological Chem., vol. 278, No. 47, pp. 46649-46653, 2003.*
Zeng, Xiao-Nong, et al. "Analysis of Characteristic Odors from Human Male Axillae" J. Chem. Ecol. (1991) 17:1469-1492.

* cited by examiner

*Primary Examiner* — Michael G Hartley
*Assistant Examiner* — Robert Cabral
(74) *Attorney, Agent, or Firm* — Martin Zhang; XuFan Tseng; Elizabeth M. Quirk

(57) ABSTRACT

The present invention provides a novel compound for counteracting amine-based malodor in consumer, industrial and textile products.

3 Claims, No Drawings

LOW VOLATILE REACTIVE MALODOR COUNTERACTIVES AND METHODS OF USE THEREOF

BACKGROUND OF THE INVENTION

Malodors are offensive odors, which are encountered in the air and on many substrates such as fabrics, hard surfaces, skin, and hair Amines, thiols, sulfides, short chain aliphatic and olefinic acids, e.g. fatty acids, are typical of the chemicals found in and contributed to sweat, household, and environmental malodors. These types of malodors typically include indole, skatole, and methanethiol found in toilet and animal odors; piperidine and morpholine found in urine; pyridine and triethyl amine found in kitchen and garbage odors; and short chain fatty acids, such as 3-methyl-3-hydroxyhexanoic acid, 3-methylhexanoic acid or 3-methyl-2-hexenoic acid, found in axilla malodors. Compounds which have been found in the axilla are described for example by Xiao-Nong Zeng, et al. (1991) *J. Chem. Ecol.* 17:1469-1492.

Malodor counteractants or masking agents have been described in the art. For example, sulthydryl reactants, such as diethyl fumarate, di-n-butyl maleate and N-ethylmaleimide are disclosed in U.S. Pat. No. 5,601,809 as compounds that are effective against axillary malodor. Further, the use of certain aromatic unsaturated carboxylic acid esters in combination with alkyl fumarates as malodor counteractants is disclosed in U.S. Pat. No. 6,610,648. U.S. Pat. No. 6,403,075 addresses fragrance materials with a phenyl ring moiety as ammonia masking agents. Similarly, US 2002/0058017 describes cis-3-hexenol to mask ammonia. Moreover, U.S. Pat. No. 7,585,833 describes methods for formulating fragrances to mask malodor present in products containing ammonia and substituted amines (See, U.S. Pat. No. 6,379,658, U.S. Pat. No. 6,376,741, U.S. Pat. No. 5,769,832, and U.S. Pat. No. 5,037,412).

Although the art describes compositions and methods for neutralizing certain malodors, there still remains a need for additional compounds that are more efficient against malodors.

SUMMARY OF THE INVENTION

The present invention features a malodor counteractant compound composed of a α-keto moiety covalently attached to a polymer, an oligomer, a surfactant, or a solid surface. In one embodiment, the α-keto moiety of the malodor counteractant compound is, for example, but not limited to, levulinic acid, acetoacetic acid, pyruvic acid, α-ketoglutaric acid, α-ketobutyric acid, α-ketoisocaproic acid, or α-ketovaleric acid. In other embodiments, the polymer is, for example, but not limited to, a polyol, polysaccharide, polyamine, polyacrylate, alkene oxide polymer, or block or random copolymer thereof; the oligomer is, for example, but not limited to, an oligosaccharide or oligomeric alkane; the surfactant is, for example, but not limited to, a poloxamine or an unbranched $C_{13}$-$C_{15}$ oxo alcohol; and the solid surface is, for example, but not limited to, a silica or clay surface. In still other embodiments, the malodor counteractant compound has the structure:

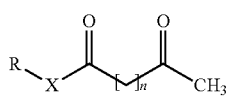

Formula I wherein X represents O, N, or C;
wherein n represents an integer of 0 or greater; and
wherein R is a polymer, an oligomer, a surfactant, or a solid surface, and wherein the polymer is (a) polyalkylene oxide with OH or $NH_2$ end groups such as polyethyleneoxide, polypropyleneoxide, polytetrahydrofuran, polyetheramine, a block or random copolymer variant thereof such as Pluronics® or Synperonics®, or a branched copolymer such as a tetronic polymer; (b) polyvinyl amine or a copolymer with vinyl formamide or vinyl acetamide; (c) polyvinyl alcohol or a copolymer with vinyl acetate, olefin such as ethylene and propylene, or acrylate; or (d) biopolymer such as polysaccharide (i.e., maltodextrin, starch, guar, xanthan, carboxymethyl cellulose, hydroxyethyl cellulose, carrageenan, or cationic/amphoteric/hydrophobically substituted polysaccharide).

Consumer, industrial and textile products containing the above malodor counteractant are also provided as are methods for producing the above malodor counteractant and using the above malodor counteractant to counteract amine-based malodor.

DETAILED DESCRIPTION OF THE INVENTION

The present invention provides compounds composed of an α-keto moiety covalently attached to a polymer, an oligomer, a surfactant (nonionic with OH, $NH_2$ or COOH groups), or a solid surface (silica or clay) for use as malodor counteractants. Advantageously, the α-keto moiety of the malodor counteractant compounds of the present invention binds to amine-based malodors thereby effectively reducing the concentration of these malodors in consumer, industrial or textile products. Moreover, the compounds of the present invention have a low vapor pressure such that the compounds can be added in significant quantities to products without impacting the olfactory character of the products. Given these features, the compounds of the present invention find use as additives to consumer products to reduce the concentration of malodors in the headspace of the product. Furthermore, the compounds of the present invention can be used to form a fragrance or flavor encapsulate or other delivery system such that while the delivery system is delivering its payload, malodors are removed from the air. Alternatively, the compounds of the present invention can be formulated into a product, such as a fragrance, which can be optionally formulated into a delivery system.

As indicated, particular embodiments feature compounds with low-to-no vapor pressure. Vapor pressure)(P°) is the pressure of a vapor of a compound in equilibrium with its pure condensed phase (solid or liquid). Vapor pressure is measured in the standard units of pressure. The International System of Units (SI) recognizes pressure as a derived unit with the dimension of force per area and designates the pascal (Pa) as its standard unit. One pascal is one Newton per square meter ($N \cdot m^{-2}$ or $kg \cdot m^{-1} \cdot s^{-2}$). Vapor pressures depend on the temperature and vary with different compounds due to differences in molecule—molecule interactions. For example, vapor pressure at 25° C. of n-alkanes is a function of chain length, wherein larger n-alkane molecules have lower P° due to greater polarizability and increased strength of London Dispersion intermolecular forces. The vapor pressure of a compound can be determined by conventional methods known to those of skill in the art. In particular embodiments, compounds of the present invention have a vapor pressure of less than 200 Pa (1.5 mmHg), less than 100 Pa (0.75 mmHg), less than 50 Pa (0.375 mmHg), less than 20 Pa (0.15 mmHg), or less than 10 Pa (0.075 mmHg), at 25° C.

The α-keto moiety of the malodor counteractant compound of the present invention is, in particular embodiments, levulinic acid, acetoacetic acid, pyruvic acid, α-ketoglutaric acid, α-ketobutyric acid, α-ketoisocaproic acid, or α-ketovaleric acid. The α-keto moiety is covalently attached to a polymer, an oligomer, a surfactant, or a solid surface. Accordingly, in certain embodiments, the malodor counteractant compound of the present invention has the structure:

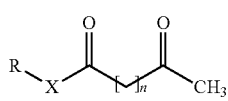

Formula I wherein X represents O, N, or C;
wherein n represents an integer of 0 or greater; and
wherein R is a polymer, an oligomer, a surfactant, or a solid surface.

A polymer in accordance with the present invention is a molecule composed of repeating monomer units. In contrast to a polymer, which can contain numerous monomers, an oligomer is a molecule that is composed of a few monomer units. In this respect, oligomers include dimers, trimers, tetramers, and the like. According to the present invention, a polymer includes, but is not limited to, a polyol (e.g., polyvinyl alcohol or a copolymer with vinyl acetate, olefin such as ethylene and propylene, or acrylate); biopolymer such as polysaccharide (e.g., maltodextrin, starch, guar, xanthan, carboxymethyl cellulose, hydroxyethyl cellulose, carrageenan, or cationic/amphoteric/hydrophobically substituted polysaccharide); polyamine (e.g., polyvinyl amine or a copolymer with vinyl formamide or vinyl acetamide); polyacrylate with alcohol groups; and polyalkylene oxide with OH or $NH_2$ end groups (e.g., polyetheramine). The polyalkylene oxide of the present invention is an alkyl ether having from 4 to 25, preferably 4-16, moles of ethylene oxide per mole of alkyl phenol (e.g., polyethylene glycol (PEG), polyethylene oxide (PEO), polypropyleneoxide, and polytetrahydrofuran) and a block or random copolymer variant thereof or a branched copolymer such as a tetronic polymer. An oligomer includes, but not limited to, e.g., oligosaccharides and oligomeric alkanes (e.g., pentanes, butanes, or hexane).

A surfactant of the present invention is a compound that lowers the surface tension of a liquid or the interfacial tension between two liquids or between a liquid and a solid. A surfactant may act as a detergent, wetting agent, emulsifier, foaming agent, or dispersant. A surfactant is usually an organic compound that is amphiphilic. Surfactants include molecules such as PLURONIC® surfactants (based on ethylene oxide, propylene oxide and/or butylenes oxide as di- and tri-block copolymers) and TETRONIC® surfactants (poloxamine or block copolymers based on ethylene oxide and propylene oxide with a vapor pressure of <0.1 mmHg at 25° C.) including TETRONIC® 901, TETRONIC® 701, TETRONIC® 904, and TETRONIC® 904, and LUTENSOL® AO nonionic surfactants (unbranched $C_{13}$-$C_{15}$ oxo alcohol) including LUTENSOL® AO3, LUTENSOL® AO4, LUTENSOL® AO5, and LUTENSOL® AO7.

A solid surface of the present invention includes, but is not limited to a silica surface (e.g., a synthetic amorphous silica surface such as SYLOID®), clay or other solid mineral materials with an appropriate functional group to attach the α-keto moiety. In another embodiment, the solid surface is the surface of a delivery system such as a nanoparticle, microparticle, nanocapsule or microcapsule, which attaches to one or more α-keto moieties.

In particular embodiments, the malodor counteractant compound of the present invention is a small molecule with no-to-low vapor pressure attached to one or more α-keto groups. In another embodiment, the malodor counteractant compound of the present invention is a polymer attached to one or more α-keto groups. In a further embodiment, the malodor counteractant compound of the present invention is an oligomer with one or more α-keto groups attached thereto. In another further embodiment, the malodor counteractant compound of the present invention is a surfactant attached to one or more α-keto groups. In still a further embodiment, the malodor counteractant compound of the present invention is a solid surface attached to one or more α-keto groups.

Specific examples of malodor counteractant compounds of the present invention include, but are not limited to, the following examples:

Formula II

Formula III

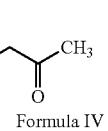

Formula IV

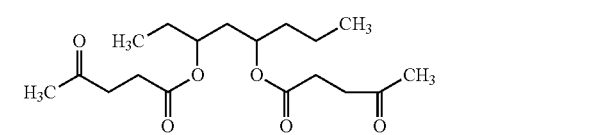

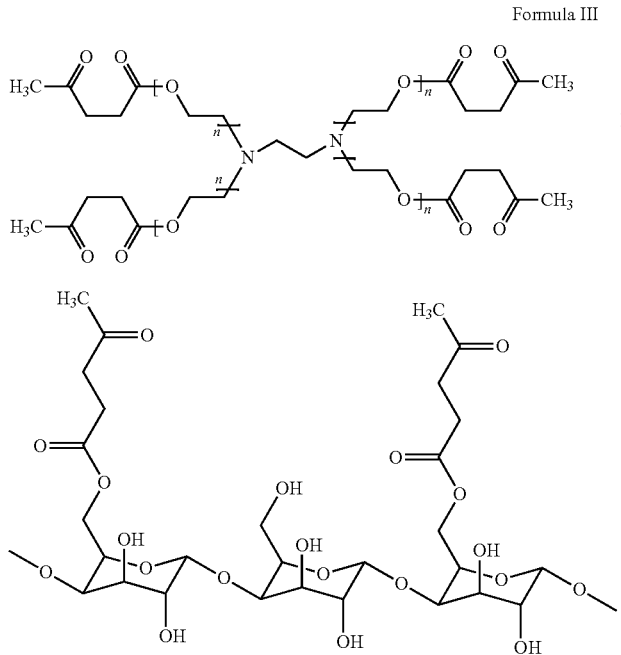

Formula V

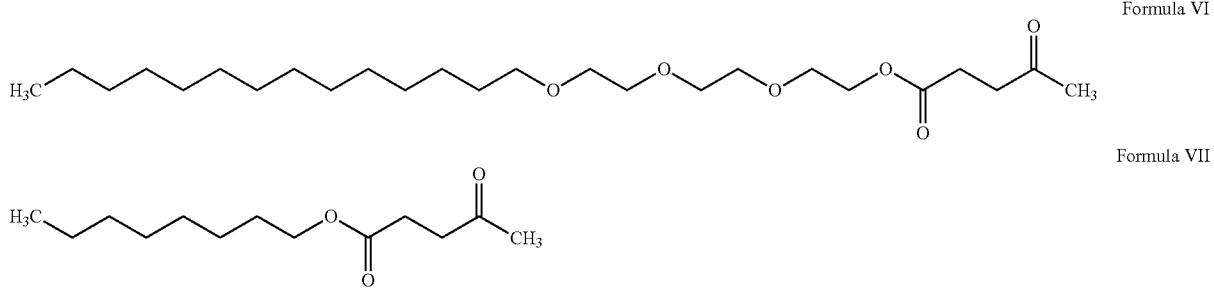

Formula VI

Formula VII

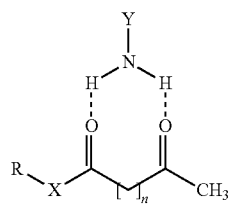

Malodor counteractant compounds of the present invention are produced by covalently attaching a α-keto moiety as described herein to a polymer, an oligomer, a surfactant, or a solid surface. Given that the α-keto moiety is covalently attached, this moiety is not released before or during use in a consumer, industrial or textile product, e.g., the compounds of the present invention are not pro-fragrances. Specific examples of reagents and reactions conditions for preparing the compounds of the present invention are provided in Examples.

The malodor counteractant compounds of the present invention can be used in a variety of forms and in a variety of products. Advantageously, the compounds of the present invention are reactive against potent malodor ingredients while not affecting the odor of a fragrance or final product. Furthermore, these compounds and the methods herein can be pursued in any situation where malodor is present. In this respect, the present invention also features a method for counteracting amine-based malodor of consumer, industrial and textile products, as well as the surrounding environment, by introducing or adding one or more malodor counteractant compounds of the present invention to a consumer, industrial or textile product so that the amine-based malodor of the product is counteracted.

The α-keto containing malodor counteractant compounds of the present invention may react with amine-based malodor molecules, for example, but not limited to, according to the following schemes:

Scheme 1: Schiff base formation

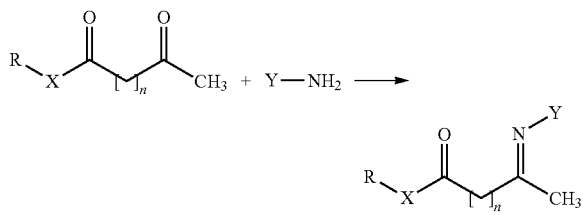

wherein X, n, and R are defined the same as above: and Y—NH$_2$ represents an amine-based malodor molecule;

Scheme 2: Hydrogen bonding or ionic interactions:

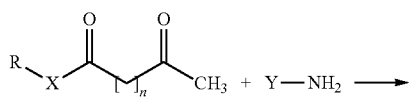

wherein X, n, R, and Y—NH$_2$ are defined the same as above.

For the purposes of the present invention, a compound counteracts a malodor if it measurably (either qualitatively or quantitatively) reduces the presence of a malodor. In particular embodiments, the malodor counteractant compounds of the present invention reduce the presence of amine-based malodor of a product by 50-100% as compared to a product that does not have the malodor counteractant compounds.

Malodors particularly targeted by the compounds of the present invention include amine-based malodor such as bathroom odors, sweat, food odors, textile odors, home care and personal care product base odors, adhesive odors, and paint odors. In this respect, the compounds of the present invention can be used in air refresheners, fabric refresheners, bar soaps, perfumes, fragrances, cologne, bath or shower gels, shampoos or other hair care products, cosmetic preparations, body odorants, deodorants, antiperspirants, liquid or solid fabric detergents or softeners, bleach products, disinfectants or all-purpose household or industrial cleaners, food, or industrial or textile products such as adhesives, paints, coatings, or textiles. In yet another embodiment, one or more of the compounds of the present invention are used as part of a delivery system or polymer system to deliver a fragrance or compound of interest (e.g., a pharmaceutical).

The following are provided as specific embodiments of the present invention. Other modifications of this invention will be readily apparent to those skilled in the art. Such modifications are understood to be within the scope of this invention. All reagents were purchased from Sigma-Aldrich, Inc. unless otherwise noted. Further, as used herein all percentages are weight percent unless otherwise noted, ppm is understood to be parts per million, L is understood to be liter, mL is understood to be milliliter, μL is understood to be microliter, mol is understood be mole, mmol is understood be millimole, and M is understood to be moles per L. IFF as used in the examples is understood to mean International Flavors & Fragrances Inc., New York, N.Y., USA.

Example I

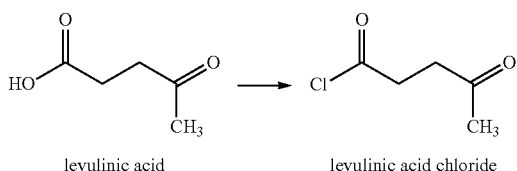

levulinic acid → levulinic acid chloride

Preparation of Levulinic Acid Chloride

Oxalyl chloride in dichloromethane (2 M, 450 mL, 0.9 mol) was added drop-wise to a stirring mixture of levulinc acid (100 g, 0.857 mol) and dimethylformamide (DMF, 2 mL) for about 1.5 to 2 hours at room temperature. After the addition was completed, the resulting mixture was stirred for additional 0.5 hours. Solvents were removed in vacuo and the crude mixture was used in subsequent reactions.

Example II

Preparation of Levulinic Tetronics (Formula III)

Triethylamine (6.91 mL, 49.50 mmol) was added to a stirring mixture of Tetronic® 901 (23.5 g, 24.77 mmol) dissolved in dichloromethane (150 mL) under nitrogen atmosphere at 0-5° C. Levulinic acid chloride (prepared as above in EXAMPLE I) was then added drop-wise. The resulting mixture was warmed to room temperature and stirred for overnight. Triethylammonium chloride salt was subsequently filtered off. The organic layer was washed with saturated $Na_2CO_3$ and concentrated in vacuo to afford the product levulinate tetronic with greater than 90% functionalization determined by NMR spectroscopy.

Example III

Preparation of Levulinate Maltrin QD® M585 Maltodextrin

Triethylamine (12.5 g, 0.124 mmol) was added to a stirring mixture of Maltrin QD® M585 maltodextrin (16.2 g, 0.100 mol) dissolved in DMF (60 mL) under nitrogen atmosphere at 0-5° C. The mole ratios of maltodextrin herein were based on monomer molecular structure of the entire polymeric chain. Levulinic acid chloride (prepared as above in EXAMPLE I) was then added drop-wise. The resulting mixture was warmed to room temperature and stirred for overnight. The triethylammonium chloride salt was subsequently filtered off. Precipitate was collected with a mixture of tetrahydrofuran (THF)/isopopanol (IPA) at a volume ratio of 1:9 (THF:IPA). The solid was filtered, washed several times with the THF:IPA mixture, and dried under vacuum to afford the product levulinate Maltrin QD® M585 maltodextrin with about 15-20% functionalization determined by NMR spectroscopy.

Example IV

Preparation of Levulinate Lutensol® AO 7

Triethylamine (11.7 g, 0.115 mol) was added to a stirring mixture of Lutensol® AO 7 (20.0 g, 57.5 mmol) dissolved in acetone (150 mL) under nitrogen atmosphere at 0-5° C. Levulinic acid chloride (prepared as above in EXAMPLE I) was then added drop-wise. The resulting mixture was warm toed room temperature and stirred for overnight. The triethylammonium chloride salt was filtered off. The solvent was concentrated in vacuo to afford the product levulinate Lutensol® AO7 with greater than 85% functionalization determined by NMR spectroscopy.

Example V

Preparation of Octyl Levulinate (Formula VII)

1-Bromooctane (332 g, 1.72 mol) was added to a stirring mixture of levulinic acid (200 g, 1.72 mol), tetrabutylammonium bromide (55.1 g, 0.17 mol), and $K_2CO_3$ (357 g, 2.58 mol) in DMF (500 mL) drop-wise and stirred at room temperature for overnight. The resulting mixture was diluted in toluene and the organic layer was washed with HCl (10%), brine, and water. The solvent was concentrated in vacuo and the oil was purified by vacuum distillation to afford the product octyl levulinate as a clear oil.

Example VI

Preparation of 4-Octyloxy Benzaldehyde

A mixture of 4-hydroxybenzaldehyde (10.0 g, 81.8 mmol), 1-bromooctane (15.8 g, 81.8 mmol), and $K_2CO_3$ (34.0 g, 0.25 mol) in DMF (150 mL) was heated to reflux for 8 hours and then cooled to room temperature. The reaction mixture was subsequently diluted in toluene. The organic layer was washed with HCl (10%), brine, and water. The solvent was concentrated in vacuo and the oil was purified by short silica gel plug (dichloromethane (DCM) in n-hexanes, 10%). Solvent was dried in vacuo to afford the product 4-octyloxy benzaldehyde as a slightly colored oil.

Example VII

Testing Procedure

The testing procedure described herein was applicable to malodor counteractant compounds containing water-soluble, modified polymers, oligomers, or surfactants.

A solution of n-butyl amine (nBA) in methanol (0.05% by weight, 500 ppm) was prepared and stored at 0° C. in a refrigerator prior to use. A solution of a malodor counteractant compound to be tested was prepared (50 to 100 mL) with distilled (DI) water and thoroughly mixed with a magnetic stir bar. The nBA solution was added to the solution of the malodor counteractant compound and the molar ratio of the malodor counteractant compound and nBA was adjusted to 1:1. For a polymer-containing malodor counteractant compound, the averaged molecular weight of the polymer was used for this calculation. Water or diethyl phthalate (DEP) containing the same amount of nBA as the test group was used as a control.

For analysis, the aqueous polymer/surfactant (1 mL) was placed into a 20 mL headspace vial using a positive displacement pipette. nBA solution (0.05%, 250 µL) was subsequently added into the vial. The vial was then capped immediately. The vial was placed in a holder and set on an orbital incubator for a pre-selected mixing/equilibration time. An aliquot of headspace above the reaction solution was then sampled and injected into the gas chromatograph for separation and detection.

Proof of Reactivity of nBA with α-Keto-Containing Molecules:

The ability of α-keto-containing molecules to reduce the amount of amine-based malodor was determined Water was used as the control. The results are presented in the following:

| α-Keto-Containing Molecules | Malodor Reduction |
|---|---|
| 2-Pentanon | 75% at 1 hour and 83% at 12 hours |
| Ethyl levulinate | 41% at 1 hour and 69% at 12 hours |
| Butyl levulinate | 39% at 1 hour and 62% at 12 hours |
| Octyl levulinate (Formula VII) | 75% at 1 hour and 78% at 12 hours |

Example VIII

Evaluation of Malodor Counteractant Compounds

The malodor counteracting effect of malodor counteractant compounds containing a α-keto moiety covalently attached to a polymer including PEG-dilevulinate, TETRONIC® 701 tetra-levulinate, and TETRONIC® 901 tetra-levulinate were evaluated following the testing procedure described as above. The mixing/equilibration time was an hour. DEP was used as the control. The results are presented in the following:

| Malodor Counteractant Compounds | Malodor Reduction |
|---|---|
| PEG-dilevulinate | 4% |
| TETRONIC ® 701 tetra-levulinate | 97% |
| TETRONIC ® 901 tetra-levulinate | 75% |

What is claimed is:

1. A malodor counteractant compound wherein the compound is a compound of the formula

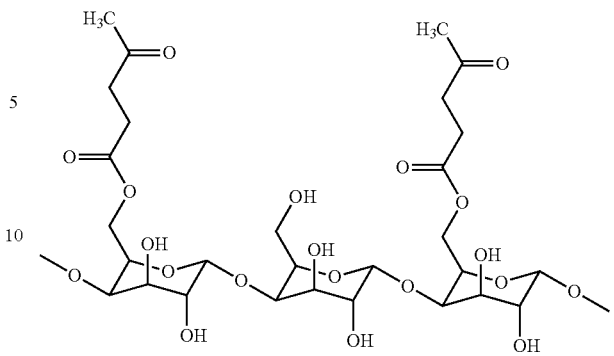

or a compound of the formula:

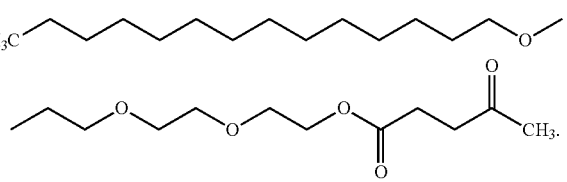

2. A consumer, industrial or textile product comprising a malodor counteractant compound of claim 1.

3. A method for counteracting an amine-based malodor of a consumer, industrial or textile product or the surrounding environment thereof comprising the step of adding the malodor counteractant compound of claim 1 to the product and reducing the presence of an amine-based malodor of the consumer, industrial or textile product.

* * * * *